United States Patent [19]

Baker et al.

[11] 4,081,468

[45] Mar. 28, 1978

[54] THIOLCARBAMATE SULFOXIDES STABILIZED WITH ACETYLENIC COMPOUNDS

[75] Inventors: Don Robert Baker, Orinda; Francis Harry Walker, Mill Valley; Chien Knei Tseng, El Cerrito, all of Calif.

[73] Assignee: Stauffer Chemical Company, Westport, Conn.

[21] Appl. No.: 721,248

[22] Filed: Sep. 8, 1976

[51] Int. Cl.$^2$ .................... C07C 147/14; A01N 9/14
[52] U.S. Cl. .................. 260/551 R; 71/103; 71/106; 560/262
[58] Field of Search ........... 260/488 H, 551 R; 71/122, 126, 106, 103; 560/262

[56] References Cited

U.S. PATENT DOCUMENTS

| | | | |
|---|---|---|---|
| 1,628,035 | 5/1927 | Denny | 71/126 X |
| 2,110,842 | 3/1938 | Ressler | 71/126 |
| 2,946,825 | 7/1960 | Monroe et al. | 71/122 X |
| 3,021,371 | 2/1962 | Watson, Jr. | 71/122 X |
| 3,070,431 | 12/1962 | Miller | 71/122 |
| 3,072,666 | 1/1963 | Watson, Jr. | 71/122 X |
| 3,535,386 | 10/1970 | Dillard | 71/122 X |
| 3,716,351 | 2/1973 | Kunkel et al. | 71/DIG. 1 X |
| 3,928,436 | 12/1975 | Tilles et al. | 260/551 R |
| 3,975,180 | 8/1976 | Gozzo et al. | 260/551 R X |
| 4,008,071 | 2/1977 | Gozzo et al. | 260/553 R X |

OTHER PUBLICATIONS

Gozzo et al., CA 82: 169773h (1975).
Kobayashi et al., CA 82: 139273c (1975).
C. S. Chem. Corp., CA 52: 10141b (1958).
Shinoda et al., CA 78: 71388d and Tanaka et al., CA 78:71389e (1973).

*Primary Examiner*—Daniel E. Wyman
*Assistant Examiner*—Thomas A. Waltz
*Attorney, Agent, or Firm*—Edith A. Rice

[57] ABSTRACT

Certain herbicidal thiolcarbamate sulfoxides can be stabilized by adding an acetylenic compound of the formula

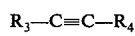

$$R_3-C\equiv C-R_4$$

wherein $R_3$ is selected from the group consisting of hydroxy, hydroxyalkyl, hydroxyalkenyl, hydroxyalkynyl, hydroxy substituted cycloalkyl, hydroxy substituted phenyl, hydroxy substituted phenalkyl, amino substituted alkyl and alkyl substituted by the group —O—C(O)-alkyl and $R_4$ is selected from the group consisting of hydrogen, alkyl, alkenyl, alkynyl, cycloalkyl, phenyl, phenalkyl, hydroxyalkyl, hydroxyalkenyl, hydroxy cycloalkyl, hydroxy substituted phenyl, hydroxy substituted phenalkyl, amino alkyl and alkyl substituted by the group —O—C(O)-alkyl.

72 Claims, No Drawings

THIOLCARBAMATE SULFOXIDES STABILIZED WITH ACETYLENIC COMPOUNDS

This invention relates to a method of improving the thermal stability of herbicidal thiolcarbamate sulfoxides and to the resulting stabilized herbicidal thiolcarbamate sulfoxide compositions.

DISCUSSION OF PRIOR ART

Thiolcarbamate sulfoxides of the type stabilized in accordance with the present invention are disclosed in U.S. Pat. Nos. 3,928,436 and 3,879,455, Belgian Pat. No. 805,839 and various other publications. While these compounds exhibit excellent herbicidal activity, they have been found to be somewhat thermally unstable. A study on the thermal stability of these compounds is reported in *The Journal of Chemistry and Industry*, Mar. 1, 1975, "On the Thermal and Chemical Stability of Carbamoyl Sulfoxides" by Gozzo, Masoero, Santi, Galluzzi and Barton. Belgian Pat. No. 829,971 to Montedison, describes crystalline carbamyl sulfoxide/urea adducts which have improved thermal stability compared to the corresponding sulfoxide.

SUMMARY OF THE INVENTION

It has now been found that the thermal stability of certain thiolcarbamate sulfoxides can be improved by combining the sulfoxide with an acetylenic compound. Accordingly, this invention comprises a novel composition of matter comprising a thiolcarbamate sulfoxide of the formula

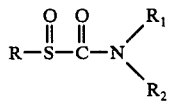

wherein R is selected from the group consisting of lower alkyl, halo lower alkyl, lower alkenyl, and alkoxy lower alkenyl; and $R_1$ and $R_2$ are independently selected from the group consisting of lower alkyl, cycloalkyl having 3-8 carbon atoms, alkylcycloalkyl, alkenyl, and alkynyl; and a stabilizing amount of an acetylenic compound.

DETAILED DESCRIPTION OF THE INVENTION

The herbicidal thiolcarbamate sulfoxides stabilized in accordance with this invention are described and claimed in U.S. Pat. No. 3,928,436 to Harry Tilles and John E. Casida. Typical compounds of this type are: S-ethyl-N,N-di-n-propyl carbamyl sulfoxide, S-ethyl-N,N-di-i-butyl carbamyl sulfoxide, S-n-propyl-N-n-butyl-N-ethyl carbamyl sulfoxide, S-ethyl-N-cyclohexyl-N-ethyl carbamyl sulfoxide, S-ethyl-N-methyl-N-α-methyl-propargyl carbamyl sulfoxide, S-n-propyl-N,N-di-n-propyl carbamyl sulfoxide, S-ethyl-N-allyl-N-n-propyl carbamyl sulfoxide, S-n-chloropropyl-N,N-diethyl carbamyl sulfoxide, S-ethoxyethenyl-N,N-di-n-propyl carbamyl sulfoxide, S-sec-butyl-N-methyl-N-cyclohexylmethyl carbamyl sulfoxide and the like.

Acetylenic compounds that can be used to stabilize thiolcarbamate sulfoxides in accordance with this invention have the general structural formula $R_3-C\equiv C-R_4$ wherein $R_3$ is selected from the group consisting of hydroxy, hydroxyalkyl, hydroxyalkenyl, hydroxyalkynyl, hydroxy substituted cycloalkyl, hydroxy substituted phenyl, hydroxy substituted phenalkyl, amino substituted alkyl and alkyl substituted by the group —O—C(O)-alkyl; and $R_4$ is selected from the group consisting of hydrogen, alkyl, alkenyl, alkynyl, cycloalkyl, phenyl, phenalkyl, hydroxyalkyl, hydroxy alkenyl, hydroxy cycloalkyl, hydroxy substituted phenyl, hydroxy substituted phenalkyl, amino alkyl and alkyl substituted by the group —O—C(O)-alkyl.

The term "alkyl" as used herein refers to straight or branched chain saturated aliphatic hydrocarbon groups of one of ten carbon atoms, e.g., methyl, ethyl, propyl, i-propyl, n-butyl, s-butyl, t-butyl, pentyl, hexyl, heptyl, nonyl, 2-methyl nonyl, decyl, and the like.

The term "alkenyl" as used herein, refers to straight and branched chain aliphatic hydrocarbon groups containing two to 10 carbon atoms and at least one carbon-carbon double bond, e.g., ethenyl, propenyl, 2-butenyl, 2-methyl-4-octenyl, and the like.

The term "alkynyl" as used herein, refers to straight and branched chain aliphatic hydrocarbon groups containing two to 10 carbon atoms and at least one carbon-carbon triple bond, e.g., ethynyl, propynyl, 2-butynyl, and the like.

The term "cycloalkyl" as used herein refers to cycloalkyl radicals containing three to eight carbon atoms, i.e., cyclopropyl, cyclobutyl, cyclopentyl, cyclohexyl, cycloheptyl, and cyclooctyl.

The term "alkoxy" as used herein refers to a straight or branched chain saturated aliphatic hydrocarbonoxy group containing one to ten carbon atoms, e.g., methoxy, ethoxy, propoxy, i-butoxy, 2-methyloctyloxy, n-decyloxy and the like.

Particularly preferred as stabilizers are acetylenic alcohols, i.e., compounds of the formula $R_3-C\equiv C-R_4$ wherein at least one of $R_3$ and $R_4$ is a hydroxy containing group. That is, compounds wherein $R_3$ is selected from the group consisting of hydroxy, hydroxy alkyl, hydroxy alkenyl, hydroxy alkynyl, hydroxy substituted cycloalkyl, hydroxy substituted phenyl, and hydroxy substituted phenalkyl; and $R_4$ is selected from the group consisting of hydrogen, alkyl, alkenyl, alkynyl, cycloalkyl, phenyl, phenalkyl, hydroxyalkyl, hydroxy alkenyl, hydroxy cycloalkyl, hydroxy substituted phenyl, and hydroxy substituted phenalkyl.

Another class of acetylenic compounds that can be utilized to stabilize thiolcarbamate sulfoxides in accordance with this invention are ethylene oxide adducts of tertiary acetylenic alcohols having the formula

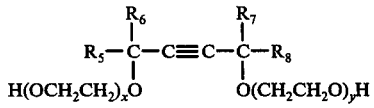

wherein $R_5$ and $R_8$ and $C_{3-10}$ alkyl and $R_6$ and $R_7$ are methyl or ethyl and $x$ and $y$ have a sum of 3–60. Ethylene oxide adducts of this type are disclosed in U.S. Pat. No. 3,293,191 to G. B. Carpenter, M. W. Leeds, and R. J. Tedeschi.

The acetylenic compounds contemplated for use in accordance with the present invention are well known compounds and many are commercially available.

Methods for preparation of acetylenic compounds are well known to those skilled in the art. See, for example, *Acetylenic Compounds in Organic Synthesis*, R. A. Raphael, New York Academic Press Inc., 1955.

Illustrative examples of acetylenic compounds are: 3-phenyl-2-propyn-1-ol, 1-phenyl-1-butyn-4-ol, 4-methyl-1-pentyn-3-ol, 2-methyl-3-pentyn-2-ol, ethynyl cyclohexanol, 3-pentyn-1-ol, 2-heptyn-1-ol, methyl butynol, 2-penten-4-yn-1-ol, 3-butyn-1-ol, 4-methyl-4-penten-2-yn-1-ol, 3-hexyn-2-ol, 3-butyn-2-ol, 2-butyn-1-ol, 3-methyl-1-pentyn-3-ol, 3-pentyn-2-ol, 2-butyn-1,4-diol, 2-butyn-1,4-diol diacetate, methyl phenyl ethynyl carbinol, 1-phenyl-1-hexyn-3-ol, monopropargylamine hydrochloride, 1,4-di-(1-hydroxy cyclohexyl) butadiyne, 1,4-dimethoxy-2-butyne, 3,6-dimethyl-1-heptyn-3-ol and the like. Other acetylene compounds for use in accordance with this invention will be readily apparent to one skilled in the art.

The novel compositions of this invention contain a thiolcarbamate sulfoxide and a stabilizing amount of acetylenic compound. The amount of acetylenic compound required for effective stabilization of the sulfoxide depends on the particular acetylenic compound and sulfoxide. Usually will be at least about 20% by weight, based on the weight of the sulfoxide. In general, the amount of acetylenic compound added should be in the range of about 20 to about 300% by weight, and preferably about 50 to about 150% by weight, based on the weight of the sulfoxide.

The following example illustrates the improvement in thermal stability of thiolcarbamate sulfoxides by the addition of acetylenic compounds.

EXAMPLE

The stability of each of S-ethyl-N,N-di-n-propyl carbamyl sulfoxide, S-n-propyl-N,N-di-n-propyl carbamyl sulfoxide, and S-ethyl-N,N-di-isobutyl carbamyl sulfoxide alone and in combination with various acetylenic compounds was tested under side-by-side testing conditions. Into separate test tubes was placed an amount of sulfoxide and the designated acetylenic compound was added. The quantities used are specified in the following tables. The test tubes were placed in a constant temperature oil bath maintained at 60° C and each connected to a manometer. Thermal decomposition of the sulfoxide was determined by measurement of the gas evolved due to decomposition of the sulfoxide over a period of about 8 hours. The amount of gas evolved by each composition was measured as the displacement in centimeters (cm) of the oil in the manometer. The results are shown in the following tables.

In Table I, the stability of 0.5 grams (g) of S-ethyl-di-n-propyl carbamyl sulfoxide with the addition of various acetylenic compounds as stabilizers is reported.

In Table II, the stability of 0.5 grams (g) of S-n-propyl-di-n-propyl carbamyl sulfoxide with the addition of various acetylenic compounds as stabilizers is reported.

In Table III, the stability of 0.5 grams (g) of S-ethyl-n-di-isobutyl carbamyl sulfoxide with the addition of various acetylenic compounds as stabilizers is reported.

In Table IV, the stability of S-ethyl-di-n-propyl carbamyl sulfoxide with varying amounts of preferred acetylenic compounds is reported.

In Table V, the stability of S-n-propyl-di-n-propyl carbamyl sulfoxide with varying amounts of preferred acetylenic stabilizers is reported.

In Table VI, the stability of S-ethyl-di-isobutyl carbamyl sulfoxide with varying amounts of preferred acetylenic stabilizers is reported.

TABLE I

Stability of S-ethyl-di-n-propyl carbamyl Sulfoxide (0.5 g) at 60° C for 8 hrs.

| Stabilizer | Amount (g) | Gas Evolved (cm) |
|---|---|---|
| Control | — | 4.7 |
| 3-phenyl-2-propyn-1-ol | 0.3 | 4.0 |
| 1-phenyl-1-butyn-4-ol | 0.4 | 1.6 |
| 4-methyl-1-pentyn-3-ol | 0.2 | 2.0 |
| 2-methyl-3-pentyn-2-ol | 0.2 | 0.1 |
| ethynyl cyclohexanol | 0.3 | 1.7 |
| 3-pentyn-1-ol | 0.2 | 2.5 |
| 2-heptyn-1-ol | 0.3 | 1.3 |
| methyl butynol | 0.2 | 0.8 |
| 2-penten-4-yn-1-ol | 0.2 | 2.4 |
| 3-butyn-1-ol | 0.2 | 2.1 |
| 4-methyl-4-penten-2-yn-1-ol | 0.2 | 2.8 |
| 3-hexyn-1-ol | 0.2 | 5.0 |
| 3-butyn-2-ol | 0.2 | 2.3 |
| Surfynol 104E[1] | 0.5 | 1.9 |
| Surfynol 440[2] | 0.3 | 1.0 |
| Surfynol 61[3] | 0.3 | 0.6 |

TABLE II

Stability of S-n-propyl-di-n-propyl carbamyl sulfoxide (0.5 g) at 60° C for 8 hrs.

| Stabilizer | Amount (g) | Gas Evolved (cm) |
|---|---|---|
| Control | — | 5.8 |
| 3-phenyl-2-propyn-1-ol | 0.3 | 3.6 |
| 1-phenyl-1-butyn-4-ol | 0.4 | 3.5 |
| 4-methyl-1-pentyn-3-ol | 0.2 | 1.9 |
| 2-methyl-3-pentyn-2-ol | 0.2 | 2.6 |
| ethynyl cyclohexanol | 0.3 | 2.2 |
| 3-pentyn-1-ol | 0.2 | 3.5 |
| 2-heptyn-1-ol | 0.3 | 2.6 |
| methyl butynol | 0.2 | 0.6 |
| 2-penten-4-yn-1-ol | 0.2 | 4.3 |
| 3-butyn-1-ol | 0.2 | 3.9 |
| 4-methyl-4-penten-2-yn-1-ol | 0.2 | 2.3 |
| 3-hexyn-1-ol | 0.2 | 3.6 |
| 3-butyn-2-ol | 0.2 | 3.1 |
| 2-butyn-1-ol | 0.2 | 3.5 |
| 3-methyl-1-pentyn-3-ol | 0.3 | 2.7 |
| 3-pentyn-2-ol | 0.2 | 6.1 |
| 2-butyn-1,4-diol | 0.2 | 7.5 |
| 2-butyn-1,4-diol diacetate | 0.4 | 5.1 |
| methyl phenyl ethynyl carbinol | 0.3 | 3.8 |
| 1-phenyl-1-hexyn-3-ol | 0.4 | 2.2 |
| monopropargylamine hydrochloride | 0.2 | 2.7 |
| Surfynol 104E[1] | 0.5 | 1.8 |

TABLE III

Stability of S-ethyl-di-isobutyl carbamyl sulfoxide (0.6 g) at 60° C for 8 hrs.

| Stabilizer | Amount (g) | Gas Evolved (cm) |
|---|---|---|
| Control | — | 3.3 |
| 3-phenyl-2-propyn-1-ol | 0.3 | 2.1 |
| 1-phenyl-1-butyn-4-ol | 0.3 | 2.0 |
| 4-methyl-1-pentyn-3-ol | 0.2 | 1.8 |
| 2-methyl-3-pentyn-2-ol | 0.2 | 0.4 |
| ethynyl cyclohexanol | 0.3 | 2.0 |
| 3-pentyn-1-ol | 0.2 | 2.1 |
| 2-heptyn-1-ol | 0.2 | 2.2 |
| methyl butynol | 0.2 | −0.9 |
| 2-penten-4-yn-1-ol | 0.2 | 3.4 |
| 3-butyn-1-ol | 0.1 | 3.0 |
| 4-methyl-4-penten-2-yl-1-ol | 0.2 | 1.7 |
| 3-hexyn-1-ol | 0.2 | 3.0 |
| 3-butyn-2-ol | 0.1 | 2.4 |
| propargyl alcohol | 0.1 | 2.7 |
| 3-methyl-1-pentyn-3-ol | 0.2 | 2.6 |
| 3-pentyn-2-ol | 0.2 | 3.1 |
| 2-butyn-1,4-diol | 0.2 | 4.3 |
| 2-butyn-1,4-diol diacetate | 0.4 | 1.7 |
| methyl phenyl ethynyl carbinol | 0.3 | 3.2 |
| 1-phenyl-1-hexyn-3-ol | 0.4 | 2.2 |
| 3,4-dimethyl-1-pentyn-3-ol | 0.2 | 4.4 |
| 3,6-dimethyl-1-heptyn-3-ol | 0.2 | 4.3 |
| 1,4-dimethoxy-2-butyne | 0.3 | 2.2 |

TABLE III-continued

Stability of S-ethyl-di-isobutyl carbamyl sulfoxide (0.6 g) at 60° C for 8 hrs.

| Stabilizer | Amount (g) | Gas Evolved (cm) |
|---|---|---|
| 1,4-di(1-hydroxycyclohexyl) butadiyne | 0.5 | 3.6 |
| 2,4,7,9-tetramethyl-5-decyn-4,7-diol | 0.3 | 4.2 |
| 2,5-dimethyl-5-hexen-3-yn-2-ol | 0.3 | 4.0 |
| monopropargylamine hydrochloride | 0.2 | 2.8 |
| Surfynol 104E[1] | 0.5 | 1.7 |

TABLE IV

Stability of S-ethyl-di-n-propyl carbamyl sulfoxide (0.5 g) at 60° C for 8 hrs.

| Stabilizer | Amount (g) | Gas Evolved (cm) |
|---|---|---|
| Control | — | 6.4 |
| 1-phenyl-1-butyn-4-ol | 0.8 | 2.7 |
| 1-phenyl-1-butyn-4-ol | 0.4 | 2.5 |
| 1-phenyl-1-butyn-4-ol | 0.2 | 3.4 |
| 2-methyl-3-pentyn-2-ol | 0.6 | 2.2 |
| 2-methyl-3-pentyn-2-ol | 0.4 | 2.2 |
| 2-methyl-3-pentyn-2-ol | 0.2 | 1.5 |
| 2-methyl-3-pentyn-2-ol | 0.1 | 3.7 |
| ethynyl cyclohexanol | 0.6 | 1.7 |
| ethynyl cyclohexanol | 0.3 | 3.0 |
| ethynyl cyclohexanol | 0.1 | 4.1 |
| 2-heptyn-1-ol | 0.6 | 2.7 |
| 2-heptyn-1-ol | 0.3 | 3.5 |
| 2-heptyn-1-ol | 0.1 | 5.3 |
| methyl butynol | 0.6 | 2.6 |
| methyl butynol | 0.4 | 2.3 |
| methyl butynol | 0.2 | 0.8 |
| methyl butynol | 0.1 | 0.9 |
| propargyl alcohol | 0.6 | 1.8 |
| propargyl alcohol | 0.4 | 2.0 |
| propargyl alcohol | 0.2 | 3.0 |
| Surfynol 104E[1] | 0.5 | 1.1 |
| Surfynol 104E | 0.3 | 0.5 |
| Surfynol 104E | 0.1 | 3.3 |
| Surfynol 440[2] | 0.5 | 1.1 |
| Surfynol 440 | 0.3 | 1.8 |
| Surfynol 440 | 0.1 | 3.5 |
| Surfynol 61[3] | 0.5 | 1.4 |
| Surfynol 61 | 0.3 | 1.5 |
| Surfynol 61 | 0.1 | 2.8 |

TABLE V

Stability of S-n-propyl-di-n-propyl carbamyl sulfoxide (0.5 g) at 60° C for 8 hrs.

| Stabilizer | Amount (g) | Gas Evolved (cm) |
|---|---|---|
| Control | — | 5.5 |
| 4-methyl-1-pentyn-3-ol | 0.5 | 1.5 |
| 4-methyl-1-pentyn-3-ol | 0.4 | 1.7 |
| 4-methyl-1-pentyn-3-ol | 0.3 | 1.9 |
| 4-methyl-1-pentyn-3-ol | 0.2 | 2.1 |
| 4-methyl-1-pentyn-3-ol | 0.1 | 3.2 |
| ethynyl cyclohexanol | 0.5 | 1.8 |
| ethynyl cyclohexanol | 0.4 | 2.5 |
| ethynyl cyclohexanol | 0.3 | 2.5 |
| ethynyl cyclohexanol | 0.2 | 3.3 |
| ethynyl cyclohexanol | 0.1 | 3.2 |
| methyl butynol | 0.5 | 1.8 |
| methyl butynol | 0.4 | 1.8 |
| methyl butynol | 0.3 | 1.5 |
| methyl butynol | 0.2 | 1.8 |
| methyl butynol | 0.1 | 2.4 |
| 4-methyl-4-penten-2-yn-1-ol | 0.5 | 0.4 |
| 4-methyl-4-penten-2-yl-1-ol | 0.4 | 0.4 |
| 4-methyl-4-penten-2-yn-1-ol | 0.3 | 1.0 |
| 4-methyl-4-penten-2-yn-1-ol | 0.2 | 2.9 |
| 4-methyl-4-penten-2-yn-1-ol | 0.1 | 3.5 |

TABLE VI

Stability of S-ethyl-di-isobutyl carbamyl sulfoxide (0.6 g) at 60° C for 8 hrs.

| Stabilizer | Amount (g) | Gas Evolved (cm) |
|---|---|---|
| Control | — | 3.0 |
| 4-methyl-1-pentyn-3-ol | 0.6 | 1.3 |
| 4-methyl-1-pentyn-3-ol | 0.4 | 1.3 |
| 4-methyl-1-pentyn-3-ol | 0.2 | 2.0 |
| 4-methyl-1-pentyn-3-ol | 0.1 | 2.4 |
| 2-methyl-3-pentyn-2-ol | 0.6 | 1.8 |
| 2-methyl-3-pentyn-2-ol | 0.4 | 2.1 |
| 2-methyl-3-pentyn-2-ol | 0.2 | −1.4 |
| 2-methyl-3-pentyn-2-ol | 0.1 | 0.3 |
| methyl butynol | 0.6 | 2.1 |
| methyl butynol | 0.4 | 1.4 |
| methyl butynol | 0.2 | −0.3 |
| methyl butynol | 0.1 | 0.6 |
| 4-methyl-4-penten-2-yn-1-ol | 0.6 | −1.7 |
| 4-methyl-4-penten-2-yn-1-ol | 0.4 | 0.5 |
| 4-methyl-4-penten-2-yn-1-ol | 0.2 | 0.7 |
| 4-methyl-4-penten-2-yn-1-ol | 0.1 | 3.1 |
| 2-butyn-1,4-diol diacetate | 0.6 | −1.0 |
| 2-butyn-1,4-diol diacetate | 0.4 | −0.6 |
| 2-butyn-1,4-diol diacetate | 0.2 | 1.4 |
| 2-butyn-1,4-diol diacetate | 0.1 | 1.3 |

[1]Surfynol 104E is a commercially available mixture of 50% 2,4,7,9-tetramethyl-4-decyn-4,7-diol in ethylene glycol.
[2]Surfynol 440 is a commercially available ethylene oxide adduct of 2,4,7,9-tetramethyl-5-decyn-4,7-diol.
[3]Surfynol 61 is 3,5-dimethyl-1-hexyn-3-ol.

In the above tables, the negative values are believed to indicate absorption of the evolved gas by the system.

The acetylenic compound can be admixed with the herbicidal thiolcarbamate sulfoxide in any conventional manner to form a stabilized herbicidal composition.

The herbicidal compositions of this invention are generally applied to soil to control the growth of undesirable vegetation in the form of formulations containing the composition and an inert carrier. Herbicidal formulations generally take the form of dusts, wettable powders, granules, solutions, or emulsifiable concentrates.

Dusts are free-flowing powder compositions containing the herbicidal composition impregnated on a particulate carrier. The particle size of the carrier is usually in the range of from about 30 to 50 microns. Examples of suitable carriers are talc, bentoinite, diatomaceous earth, and pryrophyllite. Anticaking and antistatic agents can be added, if desired. The composition generally contains up to 50% of active ingredient.

Wettable powders are finely divided compositions comprising a particulate carrier impregnated with the herbicidal composition and additionally containing one or more surface active agents. The surface active agent promotes rapid dispersion of the powder in aqueous medium to form stable, sprayable suspensions, A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in *Pesticide Formulations* by Wade Van Valkenburg, Marcel Dekker, Inc., N.Y. 1973 at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granular carrier.

Suitable carriers in preparation of granules include clay, vermiculite, sawdust, granular carbon, and the like.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate if desired.

The compositions are applied to the soil to control the growth of undesirable vegetation at a rate to provide about 1 to about 50, preferably about 1 to about 10, pounds per acre of active herbicidal ingredient. The amount of active ingredient used per acre will depend on overall cost and desired result.

What is claimed is:

1. A composition of matter comprising a thiolcarbamate sulfoxide of the formula

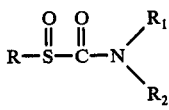

wherein R is selected from the group consisting of lower alkyl, halo lower alkyl, lower alkenyl, and alkoxy lower alkenyl; and $R_1$ and $R_2$ are independently selected from the group consisting of lower alkyl, cycloalkyl having 3-8 carbon atoms, lower alkylcycloalkyl, lower alkenyl, and lower alkynyl and a stabilizing amount of an acetylenic compound having the formula

wherein $R_3$ is selected from the group consisting of hydroxy, hydroxy alkyl, hydroxy alkenyl, hydroxy alkynyl, hydroxy substituted cycloalkyl, hydroxy substituted phenyl, hydroxy substituted phenalkyl, amino substituted alkyl and alkyl substituted by the group —O—C(O)-alkyl and $R_4$ is selected from the group consisting of hydrogen, alkyl, alkenyl, alkynyl, cycloalkyl, phenyl, phenalkyl, hydroxy alkyl, hydroxy alkenyl, hydroxy cycloalkyl, hydroxy substituted phenyl, hydroxy substituted phenalkyl, amino alkyl, and alkyl substituted by the group —O—C(O)-alkyl.

2. The composition of claim 1 wherein said acetylenic compound is of the formula

and $R_3$ is selected from the group consisting of hydroxy, hydroxy alkyl, hydroxy alkenyl, hydroxy alkynyl, hydroxy substituted cycloalkyl, hydroxy substituted phenyl, and hydroxy substituted phenalkyl; and $R_4$ is selected from the group consisting of hydrogen, alkyl, alkenyl, alkynyl, cycloalkyl, phenyl, phenalkyl, hydroxy alkyl, hydroxy alkenyl, hydroxy cycloalkyl, hydroxy substituted phenyl, and hydroxy substituted phenalkyl.

3. The composition of claim 1 wherein said thiolcarbamate sulfoxide is S-ethyl-N,N-di-n-propyl carbamyl sulfoxide.

4. The composition of claim 3 wherein said acetylenic compound is 3-phenyl-2-propyn-1-ol.

5. The composition of claim 3 wherein the acetylenic compound is 1-phenyl-1-butyn-4-ol.

6. The composition of claim 3 wherein said acetylenic compound is 4-methyl-1-pentyn-3-ol.

7. The composition of claim 3 wherein said acetylenic compound is 2-methyl-3-pentyn-2-ol.

8. The composition of claim 3 wherein said acetylenic compound is ethynyl cyclohexanol.

9. The composition of claim 3 wherein said acetylenic compound is 3-pentyn-1-ol.

10. The composition of claim 3 wherein said acetylenic compound is 2-heptyn-1-ol.

11. The composition of claim 3 wherein said acetylenic compound is methyl butynol.

12. The composition of claim 3 wherein said acetylenic compound is 2-penten-4-yn-1-ol.

13. The composition of claim 3 wherein said acetylenic compound is 3-butyn-1-ol.

14. The composition of claim 3 wherein said acetylenic compound is 4-methyl-4-penten-2-yn-1-ol.

15. The composition of claim 3 wherein said acetylenic compound is 3-hexyn-1-ol.

16. The composition of claim 3 wherein said acetylenic compound is 3-butyn-2-ol.

17. The composition of claim 3 wherein said acetylenic compound is 2,4,7,9-tetramethyl-5-decyn-4,7-diol.

18. The composition of claim 3 wherein said acetylenic compound is 3,5-dimethyl-1-hexyn-3-ol.

19. The composition of claim 1 wherein said thiolcarbamate sulfoxide is S-n-propyl-N,N-di-n-propyl carbamyl sulfoxide.

20. The composition of claim 19 wherein said acetylenic compound is 3-phenyl-2-propyn-1-ol.

21. The composition of claim 19 wherein said acetylenic compound is 1-phenyl-3-butyn-4-ol.

22. The composition of claim 19 wherein said acetylenic compound is 4-methyl-1-pentyn-3-ol.

23. The composition of claim 19 wherein said acetylenic compound is 2-methyl-3-pentyn-2-ol.

24. The composition of claim 19 wherein said acetylenic compound is ethynyl cyclohexanol.

25. The composition of claim 19 wherein said acetylenic compound is 3-pentyn-1-ol.

26. The composition of claim 19 wherein said acetylenic compound is 2-heptyn-1-ol.

27. The composition of claim 19 wherein said acetylenic compound is methyl butynol.

28. The composition of claim 19 wherein said acetylenic compound is 2-penten-4-yn-1-ol.

29. The composition of claim 19 wherein said acetylenic compound is 4-methyl-4-penten-2-yn-1-ol.

30. The composition of claim 19 wherein said acetylenic compound is 3-butyn-1-ol.

31. The composition of claim 19 wherein said acetylenic compound is 3-hexyn-1-ol.

32. The composition of claim 19 wherein said acetylenic compound is 3-butyn-1-ol.

33. The composition of claim 19 wherein said acetylenic compound is 2-butyn-1-ol.

34. The composition of claim 19 wherein said acetylenic compound is 3-methyl-1-pentyn-3-ol.

35. The composition of claim 19 wherein said acetylenic compound is 3-pentyn-2-ol.

36. The composition of claim 19 wherein said acetylenic compound is 2-butyn-1,4-diol.

37. The composition of claim 19 wherein said acetylenic compound is 2-butyn-1,4-diol diacetate.

38. The composition of claim 19 wherein said acetylenic compound is 3-methyl-1-phenyl-1-propyne-3-ol.

39. The composition of claim 19 wherein said acetylenic compound is 1-phenyl-1-hexyn-3-ol.

40. The composition of claim 19 wherein said acetylenic compounds is monopropargylamine.

41. The composition of claim 19 wherein said acetylenic compound is 2,4,7,9-tetramethyl-5-decyn-4,7-diol.

42. The composition of claim 1 wherein said thiolcarbamate sulfoxide is S-ethyl-N,N-di-isobutyl carbamyl sulfoxide.

43. The composition of claim 42 wherein said acetylenic compound is 3-phenyl-2-propyn-2-ol.

44. The composition of claim 42 wherein said acetylenic compound is 1-phenyl-1-butyn-4-ol.

45. The composition of claim 42 wherein said acetylenic compound is 4-methyl-1-pentyn-3-ol.

46. The composition of claim 42 wherein said acetylenic compound is 2-methyl-3-pentyn-2-ol.

47. The composition of claim 42 wherein said acetylenic compound is ethynyl cyclohexanol.

48. The composition of claim 42 wherein said acetylenic compound is 3-pentyn-1-ol.

49. The composition of claim 42 wherein said acetylenic compound is 2-heptyn-1-ol.

50. The composition of claim 42 wherein said acetylenic compound is methyl butynol.

51. The composition of claim 42 wherein said acetylenic compound is 2-penten-4-yn-1-ol.

52. The composition of claim 42 wherein said acetylenic compound is 3-butyn-1-ol.

53. The composition of claim 42 wherein said acetylenic compound is 4-methyl-2-penten-2yn-1-ol.

54. The composition of claim 42 wherein said acetylenic compound is 3-hexyn-1-ol.

55. The composition of claim 42 wherein said acetylenic compound is 3-butyn-2-ol.

56. The composition of claim 42 wherein said acetylenic compound is propargly alcohol.

57. The composition of claim 42 wherein said acetylenic compound is 3-methyl-1-pentyn-3-ol.

58. The composition of claim 42 wherein said acetylenic compound is 3-penten-2-ol.

59. The composition of claim 42 wherein said acetylenic compound is 2-butyn-1,4-diol.

60. The composition of claim 42 wherein said acetylenic compound is 2-butyn-1,4-diol diacetate.

61. The composition of claim 42 wherein said acetylenic compound is 3-methyl-1-phenyl-1-propyne-3-ol.

62. The composition of claim 42 wherein said acetylenic compound is 1-phenyl-1-hexyn-3-ol.

63. The composition of claim 42 wherein said acetylenic compound is 3,6-dimethyl-1-pentyn-3-ol.

64. The composition of claim 42 wherein said acetylenic compound is 3,6-dimethyl-1-heptyn-3-ol.

65. The composition of claim 42 wherein said acetylenic compound is 1,4-dimethoxy-2-butyne.

66. The composition of claim 42 wherein said acetylenic compound is 1,4-di-(1-hydroxycyclohexyl)-butadiyne.

67. The composition of claim 42 wherein said acetylenic compound is 2,4,7,9-tetramethyl-5-decyn-4,7-diol.

68. The composition of claim 42 wherein said acetylenic compound is 2,5-dimethyl-5-hexen-3-yn-2-ol.

69. The composition of claim 42 wherein said acetylenic compound is monopropargylamine.

70. A composition of matter comprising a thiolcarbamate sulfoxide of the formula

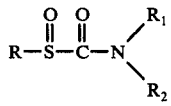

wherein R is selected from the group consisting of lower alkyl, halo lower alkyl, lower alkenyl, and alkoxy lower alkenyl; and $R_1$ and $R_2$ are independently selected from the group consisting of lower alkyl, cycloalkyl having 3-8 carbon atoms, lower alkylcycloalkyl, lower alkenyl, and lower alkynyl and a stabilizing amount of an acetylenic compound having the formula

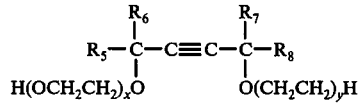

wherein $R_5$ and $R_8$ ar $C_{3-10}$ alkyl and $R_6$ and $R_7$ are methyl or ethyl and $x$ and $y$ have a sum of 3-60.

71. The composition of claim 70 wherein said thiolcarbamate sulfoxide is S-ethyl-N,N-di-n-propyl carbamyl sulfoxide and in said acetylenic compound $R_5$ and $R_8$ are isobutyl and $R_6$ and $R_7$ are methyl.

72. The composition of claim 70 wherein said thiolcarbamate sulfoxide is S-ethyl-N,N-di-isobutyl carbamyl sulfoxide and in said acetylenic compound $R_5$ and $R_8$ are isobutyl and $R_6$ and $R_7$ are methyl.

* * * * *